United States Patent [19]

Gohla et al.

[11] Patent Number: 5,750,124
[45] Date of Patent: May 12, 1998

[54] W/O/W EMULSIONS

[75] Inventors: Sven Gohla; Anja Müller, both of Hamburg; Jens Nielsen, Henstedt, all of Germany

[73] Assignee: Beiersdorf Ag, Hamburg, Germany

[21] Appl. No.: 663,138

[22] PCT Filed: Oct. 1, 1994

[86] PCT No.: PCT/DE94/01157

§ 371 Date: Jun. 17, 1996

§ 102(e) Date: Jun. 17, 1996

[87] PCT Pub. No.: WO95/17155

PCT Pub. Date: Jun. 29, 1995

[30] Foreign Application Priority Data

Dec. 22, 1993 [DE] Germany ............ 43 43 833.4

[51] Int. Cl.⁶ .................... A61K 9/113; B01J 13/00
[52] U.S. Cl. .................... 424/401; 252/312; 252/314; 514/941
[58] Field of Search .................... 252/309, 312, 252/314; 424/401; 514/941

[56] References Cited

U.S. PATENT DOCUMENTS

| | | | |
|---|---|---|---|
| 4,254,105 | 3/1981 | Fukuda | 514/941 X |
| 4,590,086 | 5/1986 | Takahashi et al. | 252/312 X |
| 4,675,179 | 6/1987 | Suzuki et al. | 514/941 X |
| 4,985,250 | 1/1991 | Bee et al. | 424/401 |
| 5,178,871 | 1/1993 | Thill | 514/941 X |
| 5,217,648 | 6/1993 | Beissinger et al. | 252/314 |
| 5,258,184 | 11/1993 | Bee et al. | 424/401 |
| 5,478,561 | 12/1995 | Ferrero | 424/401 |

FOREIGN PATENT DOCUMENTS

| | | |
|---|---|---|
| 4136699 | 10/1992 | Germany. |
| 1235667 | 6/1971 | United Kingdom. |

OTHER PUBLICATIONS

McCutcheon's Detergents and Emulsifiers, No. American Edition/1973, p.113, [TP 990.D4].

*Primary Examiner*—Richard D. Lovering
*Attorney, Agent, or Firm*—Sprung Kramer Schaefer & Briscoe

[57] ABSTRACT

Multiple emulsions of the W/O/W type having a continuous external aqueous phase, an oily phase dispersed therein and a second (internal) aqueous phase dispersed in this oily phase, comprising (a) at least one emulsifier whose lipophilicity increases with increasing temperature and the hydrophilicity of which increases with decreasing temperature, the emulsifier or emulsifiers changing from an HLB value <10 to an HLB value >10 in the temperature range of 40°–90° C., the HLB value of the emulsifier or emulsifiers at room temperature being between 11 and 18, the emulsifier not being completely soluble in the oily phase when the oily phase is combined with the aqueous phase, (b) an oily phase, the base constituent(s) being physiologically tolerated oils, fats and waxes having a "required HLB value" (RHLB) of 10–20, and/or a polarity (determined in surface tension units), individually or in combination, of less than 30 mN/m, (c) an external and an internal aqueous phase, the aqueous phases comprising 0.1–5% by weight of organic and/or inorganic electrolytes with mono-, di- or trivalent cations, (e) optionally further auxiliaries and/or additives to stabilize the multiple emulsion droplets, after in situ formation thereof, and (f) optionally other bases, auxiliaries, additives and/or active compounds customary in cosmetics or medical galenics.

25 Claims, No Drawings

W/O/W EMULSIONS

This application is 371 of PCT/DE94/01157 filed Oct. 1, 1994 which claims priority based on Fed. Rep. Germany P 4343833.4 filed Dec. 22, 1993.

The present invention relates to stable multiple emulsions of the W/O/W type, processes for their preparation and their use for cosmetic and medical purposes.

Cosmetic skin care is primarily to be understood as intensifying or re-establishing the natural function of the skin as a barrier against environmental influences (for example dirt, chemicals and microorganisms) and against the loss of endogenous substances (for example water, naturally occurring fats and electrolytes).

If this function is impaired, increased absorption of toxic or allergenic substances or attack by microorganisms and as a consequence toxic or allergic skin reactions may occur.

The aim of skin care is furthermore to compensate the loss of oils and water by the skin caused by daily washing. This is important in particular if the natural regeneration capacity is not sufficient. Furthermore, skin care products should also protect against environmental influences, in particular against sun and wind, and delay ageing of the skin.

Medical topical formulations as a rule comprise medicaments in an active concentration. For simplicity, reference is made to the legal provisions of the Federal Republic of Germany (for example cosmetics legislation, Foodstuffs and Medical Preparations Act) for a clear differentiation between cosmetic and medical use and corresponding products.

It is known that multiple emulsions—inter alia—can be distinguished by a particularly fine emulsion texture. This property is outstandingly suitable as a basis both for cosmetic and for medical topical formulations. However, where cosmetics are used only externally, all customary types of administration, for example oral administration forms, are conceivable for the medical use of emulsions.

In simple emulsions, finely dispersed droplets of the second phase (water droplets in W/O emulsions or lipid vesicles in OW emulsions) enclosed in an emulsifier shell are present in the first phase. In a multiple emulsion (second degree), on the other hand, more finely dispersed droplets of the first phase are emulsified in such droplets. Even more finely dispersed droplets may in turn also be present in these droplets (third degree multiple emulsion), and so on.

In the same way as W/O or O/W emulsions are referred to in the case of simple emulsions (Water-in-Oil or Oil-in-Water), there are W/O/W, O/W/O, O/W/O/W, W/O/W/O emulsions and so on in the case of multiple emulsions.

A W/O/W emulsion is shown in diagram form in FIG. 1, the shaded areas denoting the external and internal aqueous phase and the white areas the oily phase.

Multiple emulsions in which the particular internal and external aqueous phases or internal and external oily phases are different in nature (that is to say, for example, W/O/W' and O/W/O' emulsions) can be prepared by two-pot processes. Those emulsions in which the internal and external aqueous or oily phases are not different in nature are obtainable both by one-pot and by two-pot processes.

The multiple emulsions of the second degree are occasionally called "bimultiple systems", those of the third degree are occasionally called "trimultiple systems" and the like (W. Seifriz, Studies in Emulsions, J. Phys. Chem., 29 (1925) 738–749).

Processes for the preparation of multiple emulsions are familiar per se to the expert. Thus, there are two-pot processes in which a simple emulsion (for example a W/O emulsion) is initially introduced into the reaction vessel and is converted into a multiple emulsion (for example a W/O/W emulsion) by addition of another phase (for example an aqueous phase) with a corresponding emulsifier (for example an O/W emulsifier).

A second process comprises converting emulsifier mixtures with an oily phase and an aqueous phase into a multiple W/O/W emulsion in a one-pot process. The emulsifiers are dissolved in the oily phase and combined with the aqueous phase. A prerequisite for such a process is that the HLB values (HLB=Hydrophilic-Lipophilic-Balance) of the individual emulsifiers employed differ significantly from one another.

The definition of the HLB value for polyol fatty acid esters is given by the formula I $HLB = 20*(1-S/A)$ For a group of emulsifiers, the hydrophilic content of which comprises only ethylene oxide units, formula II applies $HLB = E/5$ wherein
S=saponification number of the ester,
A=acid number of the acid recovered
E=weight content of ethylene oxide (in %) in the total molecule.

Emulsifiers having HLB values of 6–8 are in general W/O emulsifiers, and those having HLB values of 8–18 are in general O/W emulsifiers.

Literature: "Kosmetik—Entwicklung, Herstellung und Anwendung kosmetischer Mittel" [Cosmetics—development, preparation and use of cosmetic agents]; W. Umbach (Editor), Georg Thieme Verlag 1988.

Hydrophilic emulsifiers (having high HLB values) are as a rule O/W emulsifiers. Hydrophobic or lipophilic emulsifiers (having low HLB values) are accordingly as a rule W/O emulsifiers.

U.S. Pat. No. 4,931,210 describes a process for the preparation of W/O/W emulsions in which polyglycerol polyricinoleates are used as emulsifiers.

Although multiple emulsions are thus known per se and there are entirely simple processes for their preparation, there has nevertheless to date been a lack of such systems which are stable microscopically over relatively long storage times (for example over several years) or in a wide temperature range (for example from −10° C.) or towards extreme variations in temperature (stable to swings, for example from −15° to +50° C.). This means that the multiple emulsions of the prior art convert into simple W/O or O/W emulsions with time, that is to say have a low storage stability in the sense of multiplicity. This is a disadvantage in particular since these conversion products result in an extremely inhomogeneous droplet size distribution.

At best, such conversion products are unattractive or inelegant from the cosmetic aspect. Often, however, a lack of macroscopic stability, that is to say stability to decomposition into separate phases, is also associated with the inhomogeneous size distribution of the droplets.

In this respect also, the conventional multiple emulsions were always either inadequately stable, or the transfer from the laboratory scale to large-scale industrial production was not realizable.

According to the doctrine of DE-OS 41 31 678 or WO92/18227, stable multiple emulsions, in particular W/O/W emulsions, can be obtained if emulsifier mixtures which comprise at least in each case one hydrophobic and one hydrophilic emulsifier are used.

These specifications describe processes for the preparation of stable multiple emulsions, characterized in that the hydrophilic emulsifiers are incorporated into the aqueous phase and the hydrophobic emulsifiers are incorporated into the oily phase and the two phases are then combined with one another.

Following this doctrine, it is indeed possible to achieve cosmetically elegant multiple emulsions, in particular stable W/O/W emulsions, in a relatively simple manner, but here also improvements would be desirable.

The prior art knows only those one-pot processes for the preparation of multiple emulsions, which are prepared using special pairs of emulsifiers, in which the lipophilic emulsifier is incorporated into the fatty phase and the hydrophilic emulsifier is incorporated into the aqueous phase. One-pot processes in which, using a single emulsifier, stable emulsions of the W/O/W type are obtainable were unknown to date.

It is known that as the temperature increases, hydrophilic emulsifiers change their solubility properties from water-soluble to fat-soluble. The temperature at which the emulsifiers change their solubility is called the phase inversion temperature (PIT).

S. Matsumoto (Journal of Colloid and Interface Science, Vol. 94 No. 2, 1983) reports that the development of a W/O/W emulsion precedes a phase inversion of concentrated W/O emulsions stabilized by Span 80, a distinctive W/O emulsifier. Matsumoto starts here from an extremely non-polar oil, that is to say liquid paraffin. Furthermore, a certain amount of hydrophilic emulsifiers is said to be necessary for development of a W/O/W emulsion from a W/O emulsion.

T. J. Lin, H. Kurihara and H. Ohta (Journal of the Society of Cosmetic Chemists 26, pages 121–139, March 1975) show in the case of non-polar oils that extremely unstable multiple emulsions may exist in the region of the PIT.

The object of the present invention was thus to provide stable multiple emulsions and to eliminate the disadvantages of the formulations of the prior art.

Another object of the present invention was thus to eliminate these deficiencies of the prior art and to develop processes which lead to stable multiple emulsions of high multiplicity even if a single emulsifier is used.

It was furthermore the object of the invention to develop processes which enable multiple emulsions having the advantageous properties sought to be prepared in a controlled way in a simple manner.

Finally, the object of the invention was to develop those processes which would also lead to reproducible stable W/O/W emulsions on a large industrial scale.

It has been found, surprisingly, and therein lies the achievement of the objects, that multiple emulsions of the W/O/W type consisting of a continuous external aqueous phase, an oily phase dispersed therein and a second (internal) aqueous phase dispersed in this oily phase, comprising (a) at least one emulsifier (emulsifier A), chosen from the group consisting of emulsifiers, the lipophilicity of which increases with increasing temperature and the hydrophilicity of which increases with decreasing temperature, the emulsifier or emulsifiers changing from an HLB value<10 to an HLB value>10 in the temperature range of 40°–90° C., the HLB value of the emulsifier or emulsifiers at room temperature being between 11 and 18, preferably between 13 and 14, and the emulsifier not being completely soluble in the oily phase when the oily phase is combined with the aqueous phase, (b) an oily phase, the base constituents of the oily phase being chosen from the group consisting of physiologically tolerated oils, fats and waxes which have, in themselves and/or in combination, a "required HLB value" (RHLB) of 10–20, and/or where the base constituents of the oily phase are chosen from the group consisting of physiologically tolerated polar oils, fats and waxes, the polarity of the base constituent or constituents, individually or in combination, being less than 30 mN/m (determined in surface tension units), (d) an external and an internal aqueous phase, these aqueous phases comprising 0.1–5% by weight (based on the total composition) of organic and/or inorganic electrolytes with mono-, di- or trivalent cations, (e) if desired further auxiliaries and/or additives, the chief purpose of which is to stabilize the multiple emulsion droplets, after in situ formation thereof, and which can be incorporated into the oily phase and/or the aqueous phases, (f) if desired other bases, auxiliaries, additives and/or active compounds customary in cosmetics or medical galenics, which can be incorporated into the oily phase and/or the aqueous phases.

Advantageous emulsifiers A here are mixtures of lecithin, fatty alcohols and fatty acids such as are obtainable, for example, under the trade name Biophilic S.

Sucrose fatty acid esters having the corresponding properties are likewise advantageous emulsifiers A, in particular sucrose laureate, for example obtainable under the trade name Grilloten K87.

Other advantageous emulsifiers are chosen from the group consisting of polyglycerol mono-fatty acid esters. Polyglycerol isostearate, for example obtainable under the trade name Polydermanol GE-14, and decaglyceryl monoisostearate, for example obtainable under the name Decaglyn 1-IS, have proved to be favourable representatives of this group of substances.

A dimethicone copolyol such as is obtainable under the name DC 193 is likewise advantageously to be used.

A particularly advantageous embodiment of the present invention consists of multiple emulsions of the W/O/W type comprising a continuous external aqueous phase, an oily phase dispersed therein and a second (internal) aqueous phase dispersed in this oily phase, comprising (a) at least one emulsifier of the general formula

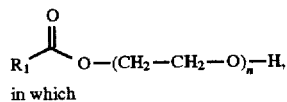

(emulsifier A)

in which $R^1 = C_{10-30}$-alkyl and
n=a number from 8 to 200, (b) an oily phase, the base constituents of the oily phase being chosen from the group consisting of physiologically tolerated oils, fats and waxes which have, in themselves and/or in combination, a "required HLB value (RHLB) of 10–20, and/or where the base constituents of the oily phase are chosen from the group consisting of physiologically tolerated polar oils, fats and waxes, the polarity of the base constituent or constituents, individually or in combination, being less than 30 mN/m, (d) an external and an internal aqueous phase, these aqueous phases comprising 0.1–5% by weight (based on the total composition) of organic and/or inorganic electrolytes with mono-, di- or trivalent cations, (e) if desired further auxiliaries and/or additives, the chief purpose of which is to stabilize the multiple emulsion droplets, after formation thereof, and which can be incorporated into the oily phase and/or the aqueous phases, (f) if desired other bases, auxiliaries, additives and/or active compounds customary in cosmetics or medical galenics, which can be incorporated into the oily phase and/or the aqueous phases.

Advantageous emulsifiers A are, for example, ethoxylated $C_{14-22}$-fatty acids having a degree of ethoxylation n which is at least 8.

Examples of advantageous emulsifiers are PEG 30-stearate, PEG 40-stearate, PEG 50-stearate and/or PEG 100-stearate, that is to say in which n=30, 40, 50 or 100 respectively and $R^1$=heptadecyl. The expert of course knows that the degree of ethoxylation n is not a discrete value but assumes a certain band width in the corresponding products. Products having a high content of emulsifiers in which the average degree of ethoxylation n assumes values from about 30 to 40 are particularly advantageous.

Emulsifiers A having HLB values which are at least 10 are particularly advantageous.

According to the formula II stated above, the values calculated are for PEG 30-stearate: an HLB value of about 16.5 for PEG 40-stearate: an HLB value of about 17.2 for PEG 50-stearate: an HLB value of about 17.7 for PEG 100-stearate: an HLB value of about 18.7.

These values are characteristic of distinctively hydrophilic emulsifiers having—under standard emulsion conditions—good O/W emulsifier properties.

Emulsifier A is advantageously employed in concentrations of 0.05–10.0% by weight, preferably in concentrations of 0.1–5.0% by weight, particularly preferably in concentrations of 0.5–2.0% by weight, in each case based on the total weight of the formulations.

A so-called "required HLB value" (called RHLB in this patent application) is often established for substances to be emulsified. This means that a substance having an RHLB value of, for example, 15 can be emulsified in water by an emulsifier having the HLB value 15. Table 1 lists frequently emulsified substances whose RHLB is between 10 and 20. The RHLB range between 10 and 20 is preferred according to the invention.

TABLE 1

| | |
|---|---|
| alcohol, cetyl | 15–16 |
| alcohol, decyl | 15 |
| alcohol, hexadecyl | 11–12 |
| alcohol, isodecyl | 14 |
| alcohol, isohexadecyl | 11–12 |
| alcohol, lauryl | 14 |
| alcohol, oleyl | 13–14 |
| alcohol, stearyl | 15–16 |
| alcohol, tridecyl | 14 |
| ethyl benzoate | 13 |
| butyl stearate | 11 |
| carnauba wax | 15 |
| decyl acetate | 11 |
| diethylaniline | 14 |
| ethylaniline | 13 |
| fenchone | 13 |
| glyceryl monostearate | 13 |
| isopropyl myristate | 13 |
| isopropyl lanolate | 14 |
| isopropyl palmitate | 11–12 |
| pine needle oil | 16 |

TABLE 1-continued

| | |
|---|---|
| lauric acid | 16 |
| maize oil | 10 |
| linoleic acid | 16 |
| menhaden oil | 12 |
| methylphenyl silicone | 11 |
| mineral oil, naphthenic (light) | 11–12 |
| mineral oil, paraffin-based | 10 |
| mineral oil, (light) | 10–11 |
| oleic acid | 17 |
| palm oil | 10 |
| PEG 30-cetyl ether | 10–11 |
| petroleum | 14 |
| polyethylene wax | 15 |
| propylene, tetramer | 14 |
| castor oil | 14 |
| ricinoleic acid | 16 |
| block paraffin | 10 |

It is particularly preferable according to the invention to choose the RHLB of the oil component or oil components from the range from 10 to 18, in particular from 13 to 16. An RHLB of about 14 is especially preferred.

The required properties of the base constituents of the oily phase can optionally, but not necessary alternatively, also be specified such that certain polarities are chosen.

Oils and fats differ, inter alia, in their polarity, which is difficult to define. It has already been proposed to adopt the surface tension with respect to water as a measure of the polarity index of an oil or an oily phase. In this case, the polarity of the oily phase in question is greater, the lower the surface tension between this oily phase and water. According to the invention, the surface tension is regarded as a possible measure of the polarity of a given oil component.

Surface tension is that force which acts on an imaginary line of one meter in length in the interface between two phases. The physical unit for this surface tension is conventionally calculated according to the force/length relationship and is usually stated in mN/m (millinewtons divided by meters). It has a positive symbol if it endeavours to reduce the interface. In the reverse case, it has a negative symbol.

According to the invention, 30 mN/m is regarded as the limit below which an oily phase is "polar" and above which an oily phase is "non-polar".

The oily phase is chosen according to the invention from the group consisting of polar oil components which have a polarity of between 10 and 30 mN/m.

Advantageous embodiments of the present invention are obtained if the oily phase is chosen from the group consisting of polar oil components, particularly preferably from the group of oil components which have a polarity of between 10 and 20 mN/m.

It is therefore particularly advantageous if the oil components fulfil both the conditions defined in the limits imposed, as described above for the RHLB and for the polarity. However, the advantageous oil components in an individual case can assume numerical values for the RHLB and polarity such that the value for one phenomenon lies in the range claimed according to the invention but the value for the other phenomenon does not.

The advantage according to the invention of using polar oils lies in the fact that these oils promote the formation of the W/O/W emulsion.

It is advantageous to use polar vegetable oils as the main component of the oily phase. The vegetable oils can advantageously be chosen from the group consisting of oils of the plant families Euphorbiaceae, Poaceae, Fabaceae, Brassicaceae, Pedalaceae, Asteraceae, Linaceae, Flacourticaceae and Violales, preferably chosen from the group of naturally occurring castor oils, wheatgerm oil, coconut oil, safflower oil, thistle oil, evening primrose oil and other oils which comprise at least 1.5% by weight of linoleic acid glycerides.

It is furthermore advantageous to employ, in addition to the emulsifier or emulsifiers A, one or more stabilizers of the general formula

in which
one of the radicals X or Y is a hydrogen atom and the remaining radical Y or X is chosen from the group consisting of branched or unbranched acyl radicals having 10–30 carbon atoms.

Stabilizer 1 is to be regarded as a lipophilic matrix-forming agent. Glycerol monostearate is preferably chosen as stabilizer 1.

It is furthermore of considerable advantage to incorporate into the oily phase one or more branched and/or unbranched aliphatic fatty alcohols and/or fatty acids having 8 to 18 carbon atoms, in particular having 16 carbon atoms, that is to say cetyl alcohol.

The unbranched aliphatic fatty alcohols and/or fatty acids having 8 to 18 carbon atoms (stabilizer 2) also do not contribute or do not contribute to a substantial degree to the formation of the multiple emulsion droplets, but stabilize macroscopically the multiple emulsion droplets already formed.

Hydrophilic matrix-forming agents can advantageously be used as a further optional stabilizer 3.

Hydrophilic matrix-forming agents are acrylates, and also naturally occurring, synthetic or semi-synthetic polysaccharides or proteins or derivatives thereof, for example xanthan gum or hydroxypropylguar gum or collagen and the like.

According to the invention, the stabilizer or stabilizers 1, 2 and/or 3 do not contribute or do not contribute to a substantial degree to the formation of the multiple emulsion droplets, but stabilize the multiple emulsion droplets already formed.

Stabilizers 1, 2 and 3 can indeed be used in the W/O/W emulsions according to the invention in any desired combination with one another, but also in each case by themselves.

However, if these stabilizers are used individually or as two-component combinations, the numbering indicates that stabilizer 1 is preferred over stabilizers 2 and 3, and stabilizer 2 is preferred over stabilizer 3.

It was astonishing and not foreseeable that by using a single emulsifier (that is to say emulsifier A), which furthermore has pronounced O/W emulsifier properties and is employed in the oily phase and only in this, stable multiple emulsions having extremely advantageous properties can be obtained.

It was furthermore not foreseeable that stable W/O/W emulsions can be prepared in one-pot processes under the conditions according to the invention.

Homogenization of the emulsion, after combining the phases, at between 40° and 80° C. surprisingly controls the droplet size of the multiple droplets, but without influencing the multiplicity of the system.

Finally, it was astonishing that a considerable increase in the stability of the W/O/W emulsions obtained according to the invention is possible with the (in itself optional) use of stabilizers of types 1, 2 and 3, these likewise being employed in the oily phase, and only in this.

The stabilizer or stabilizers 1, 2 and 3 are favourably employed in concentrations of 0.05–15.0% by weight, preferably in concentrations of 0.1–7.5% by weight, particularly preferably in concentrations of 0.5–5.0% by weight, in each case based on the total weight of the formulations.

It is furthermore of advantage to employ hydrophilic and/or lipophilic gel-forming agents. Although as a rule these do not contribute towards the formation of multiple droplets, they promote the stability of multiple droplets once formed.

The addition of electrolytes has the effect of changing the solubility properties of a hydrophilic emulsifier at the PIT if it is employed in a polar oily phase with the properties described above. The hydrophilic emulsifiers with the structures or properties described above pass through a partial phase inversion in which solubilization of water by the polar oily phase occurs, resulting in a microscopically stable W/O/W emulsion.

The W/O/W emulsions according to the invention therefore comprise electrolytes, in particular one or more salts having the following anions: chlorides, and further inorganic oxo element anions, and of these in particular sulphates, carbonates, phosphates, borates and aluminates. Electrolytes based on organic anions can also advantageously be used, for example lactates, acetates, benzoates, propionates, tartrates, citrates and many others. Comparable effects are also to be achieved by ethylenediaminetetraacetic acid and salts thereof.

Cations which are preferably used for the salts are ammonium, alkylammonium, alkali metal, alkaline earth metal, magnesium, iron and zinc ions. It does not need mentioning per se that only physiologically acceptable electrolytes should be used in cosmetics. On the other hand, specific medical uses of the W/O/W emulsions according to the invention can, at least in principle, necessitate the use of electrolytes which should not be used without medical supervision.

Potassium chloride, sodium chloride, magnesium sulphate, zinc sulphate and mixtures thereof are particularly preferred. Salt mixtures such as occur in the naturally occurring salt from the Dead Sea are likewise advantageous.

The concentration of the electrolyte or electrolytes should be about 0.1–10.0% by weight, particularly advantageously about 0.3–8.0% by weight, based on the total weight of the formulation.

It is furthermore particularly advantageous if the oily phase comprises no components which have a melting point below 40° C.

The cosmetic formulations according to the invention can comprise cosmetic auxiliaries such as are usually used in such formulations, for example preservatives, bactericides, substances having a deodorizing action, antiperspirants, insect repellants, vitamins, agents for preventing foaming, dyestuffs, pigments having a colouring action, thickeners, softening substances, moistening and/or humectant substances, fats, oils, waxes or other customary constituents of a cosmetic formulation, such as alcohols, polyols, polymers, foam stabilizers, electrolytes, organic solvents or silicone derivatives.

The formulations according to the invention can advantageously furthermore comprise substances which absorb UV radiation in the UVB range, the total amount of filter substances being, for example, 0.1% by weight to 30% by weight, preferably 0.5 to 10% by weight, in particular 1 to 6% by weight, based on the total weight of the formulation, in order to provide cosmetic formulations which protect the skin from the entire range of ultraviolet radiation. They can also be used as sunscreen compositions.

According to the invention, the W/O/W emulsions advantageously comprise one or more antioxidants. All naturally occurring, synthetic and/or semi-synthetic antioxidants which are suitable or customary for cosmetic and/or dermatological applications can be used as antioxidants which are favourable but nevertheless optionally to be used.

The antioxidants are particularly advantageously chosen from the group consisting of amino acids (for example glycine, histidine, tyrosine and tryptophan) and derivatives thereof, imidazoles (for example urocaninic acid) and derivatives thereof, peptides, such as D, L-carnosine, D-carnosine, L-carnosine and derivatives thereof (for example anserine), carotinoids, carotenes (for example α-carotene, β-carotene and lycopene) and derivatives thereof, liponic acid and derivatives thereof (for example dihydroliponic acid), aurothioglucose, propylthiouracil and other thiols (for example thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearylthiodipropionate, thiodipropionic acid and derivatives thereof (esters, ethers, peptides, lipids, nucleotides, nucleosides and salts) and sulphoximine compounds (for example buthionine-sulphoximines, homocysteine-sulphoximines, buthionine-sulphones and penta-, hexa- and heptathionine-sulphoximine) in very low tolerated dosages (for example pmol to µmol/kg), and furthermore (metal) chelators (for example α-hydroxy-fatty acids, palmitic acid, phytic acid and lactoferrin), α-hydroxy acids (for example citric acid, lactic acid and malic acid), humic acid, bile acid, bile extracts, bilirubin, biliverdin, EDTA, EGTA and derivatives thereof, unsaturated fatty acids and derivatives thereof (for example γ-linolenic acid, linoleic acid and oleic acid), folic acid and derivatives thereof, ubiquinone and ubiquinole and derivatives thereof, vitamin C and derivatives (for example ascorbyl palmitates, Mg ascorbyl phosphate and ascorbyl acetates), tocopherols and derivatives (for example vitamin E acetate), vitamin A and derivatives (for example vitamin A palmitate) and coniferyl benzoate of benzoin resin, flavones or flavonoids, rutic acid and derivatives thereof, ferulic acid and derivatives thereof, butylated hydroxytoluene, butylhydroxyanisole, nordihydroguaiac resin acid, nordihydroguaiaretic acid, trihydrobutyrophenone, furic acid, and derivatives thereof, mannose and derivatives thereof, zinc and derivatives thereof (for example ZnO and ZnSO$_4$), selenium and derivatives thereof (for example seleniummethionine), stilbenes and derivatives thereof (for example stilbene oxide and trans-stilbene oxide) and the derivatives of these active compounds mentioned which are suitable according to the invention (salts, esters, ethers, sugars, nucleotides, nucleosides, peptides and lipids).

It is furthermore of advantage to add to the W/O/W emulsions according to the invention vitamins, enzymes, coenzymes, in particular biotin or biotin esters, and also other substances of this type or a related type which are customary in cosmetics and dermatology, for example activators, such as citric acid.

Emulsions according to the invention, for example in the form of a sunscreen cream, a sunscreen lotion or a sunscreen milk, are advantageous and comprise, for example, the fats, oils, waxes and other fatty substances mentioned as well as water.

In following the doctrine according to the invention, it is possible to adjust the ratio of the total weight of the oily phase to the total weight of the sum of the two aqueous phases in the range from 10:90 to 50:50.

It is possible to establish, by suitable buffers, any pH acceptable for cosmetic or dermatological purposes without the stability of the emulsions according to the invention suffering as a result, for example in the pH interval of 3–8.5.

If the emulsions according to the invention comprise UVB filter substances, these can be oil-soluble or water-soluble. Oil-soluble UVB filters which are advantageous according to the invention are, for example:

3-benzylidenecampher derivatives, preferably 3-(4-methylbenzylidene)campher and 3-benzylidenecampher;

4-aminobenzoic acid derivatives, preferably (2-ethylhexyl)4-(dimethylamino)benzoate and amyl 4-(dimethylamino)benzoate;

esters of cinnamic acid, preferably 2-ethylhexyl 4-methoxycinnamate and isopentyl 4-methoxycinnamate;

esters of salicylic acid, preferably 2-ethylhexyl salicylate, 4-isopropylbenzyl salicylate and homomenthyl salicylate;

derivatives of benzophenone, preferably 2-hydroxy-4-methoxybenzophenone, 2-hydroxy-4-methoxy-4'-methylbenzophenone and 2,2'-dihydroxy-4-methoxybenzophenone;

esters of benzalmalonic acid, preferably di(2-ethylhexyl) 4-methoxybenzalmalonate; and 2,4,6-trianilino-(p-carbo-2'-ethyl-1'-hexyloxy)-1,3,5-triazine.

Advantageous water-soluble UVB filters are, for example:

salts of 2-phenylbenzimidazole-5-sulphonic acid, such as its sodium, potassium or its triethanolamonium salt, and the sulphonic acid itself;

sulphonic acid derivatives of benzophenones, preferably 2-hydroxy-4-methoxybenzophenone-5-sulphonic acid and its salts; and sulphonic acid derivatives of 3-benzylidenecampher, such as, for example, 4-(2-oxo-3-bornylidenemethyl) benzenesulphonic acid, 2-methyl-5-(2-oxo-3-bornylidenemethyl)benzenesulphonic acid and their salts.

If the emulsions according to the invention comprise UVA filter substances, these can advantageously be chosen according to the invention from the group consisting of derivatives of dibenzoylmethane, in particular 1-(4'-tert-butylphenyl)-3-(4'-methoxyphenyl)propane-1,3-dione and 1-phenyl-3-(4'-isopropylphenyl)propane-1,3-dione.

The formulations according to the invention can also comprise inorganic pigments which are usually used in cosmetics for protecting the skin from UV rays. These are oxides of titanium, zinc, iron, zirconium, silicon, manganese, aluminium and cerium and mixtures or modifications thereof. The pigments are particularly preferably those based on titanium dioxide.

Those cosmetic and dermatological formulations which are in the form of a sunscreen composition or a pre-sun or after-sun product are also advantageous. These advantageously additionally comprise at least one UVA filter and/or at least one UVB filter and/or at least one inorganic pigment.

Precisely those cosmetic and dermatological formulations which are in the form of a sunscreen composition or a pre-sun or after-sun product and comprise one or more antioxidants, in addition to the UVA filter or filters and/or the UVB filter or filters and/or the inorganic pigment or pigments are furthermore particularly advantageous.

The W/O/W emulsions according to the invention can in principle fulfil all cosmetic intended uses which emulsions must usually fulfil, for example day creams, night creams, hand or body creams, sunscreen formulations, nutrient creams, liposome creams, vitamin creams and the like.

It is advantageous here to use the W/O/W emulsions according to the invention both in the field of care cosmetics and in the field of decorative cosmetics.

Where appropriate, however, it is also advantageous also to use emulsions according to the invention as a carrier substance of dermatological or topical formulations.

The invention furthermore relates to a process for the preparation of W/O/W emulsions, characterized in that water containing 0.1–5% by weight (based on the total composition) of organic and/or inorganic electrolytes having mono-, di- and/or trivalent cations, and an oily phase, this oily phase comprising (a) at least one emulsifier (emulsifier A) chosen from the group consisting of emulsifiers of which the lipophilicity increases with increasing temperature and the hydrophilicity increases with decreasing temperature, the emulsifier or emulsifiers changing from an HLB value<10 to an HLB value>10 in the temperature range of 40°–90° C., the HLB value of the emulsifier or emulsifiers at room temperature being between 11 and 18, in particular 13 and 14, and the emulsifier not being completely soluble in the oily phase when the oily phase is combined with the aqueous phase, in particular at least one emulsifier of the general formula

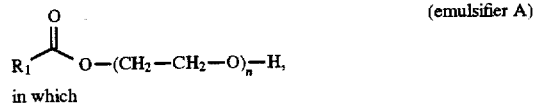

(emulsifier A)

in which $R^1 = C_{10-30}$-alkyl and
n=a number from 8 to 200.

(b) if desired furthermore comprising:
(b1) one or more stabilizers of the general formula

(stabilizer 1)

in which
one of the radicals X or Y is a hydrogen atom and the remaining radical Y or X is chosen from the group consisting of branched or unbranched acyl radicals having 10–30 carbon atoms, and/or
(b2) one or more branched and/or unbranched aliphatic fatty alcohols having 8 to 18 carbon atoms, in particular having 16 carbon atoms, that is to say cetyl alcohol, (c) the base components of this oily phase, where the base constituents of the oily phase are chosen from the group consisting of physiologically tolerated oils, fats and waxes which, in themselves and/or in combination, have a required HLB value (RHLB) of 10–20, and/or where the base constituents of the oily phase are chosen from the group consisting of physiologically tolerated polar oils, fats and waxes, the polarity of the base constituent or constituents, individually or in combination, being less than 30 mN/m, are brought together at a temperature at which the oily phase and the aqueous phase are essentially in liquid form, and the mixture thus formed is agitated constantly and if appropriate subjected to one or more homogenizing steps, and the W/O/W emulsion thus formed is then allowed to cool to room temperature.

A process according to the invention in which the W/O/W emulsion is prepared at a temperature which is above the phase inversion temperature (PIT) and is then brought to a temperature below the PIT is especially advantageous.

It lies here within the general expert knowledge of the expert and requires no inventive step at all to determine the PIT for a given emulsifier or a given emulsifier system in a given aqueous/oily phase system.

A temperature range of about 40°–90° C. can be stated as a general guideline for the PIT at customary emulsifier concentrations. In general, the PIT drops as the emulsifier concentration increases.

If desired, the bases, auxiliaries, additives and/or active compounds customary in cosmetics or medical galenics can furthermore be added during this process. The time at which such substances can be added to the process without the properties of the W/O/W emulsion to be achieved being substantially impaired is clear to the expert.

For example, and this can prove to be particularly advantageous where appropriate, the external aqueous phase can be given a different composition to the internal aqueous phase by subsequently incorporating watersoluble substances, including oils, into the W/O/W emulsion already formed. If the framework conditions known to the expert are adhered to, there is no change here in the stability or structure of the emulsion.

A process for the preparation of O/W emulsions from polar oil substances is indeed described in WO 93/11865, characterized in that a polar oil substance is emulsified with a nonionic emulsifier (having an HLB value of 10 to 18), an interface moderator (chosen from the group consisting of tocopherols and other substances) and if appropriate with a co-emulsifier from the group consisting of fatty alcohols and partial esters of polyols with fatty acids in the presence of 8 to 85% by weight of water at a temperature above the melting point of the mixture of the components, and the emulsion is heated to a temperature above the PIT or the emulsion is prepared at this temperature and the emulsion is then cooled to a temperature below the PIT.

However, merely only O/W emulsions are obtained by the process described in WO 93/11865.

Using the components according to the invention, no complete phase inversion, but only partial phase inversion, occurs in the process according to the invention. The end product is multilamellar phases of stabilized W/O/W droplets.

If W/O/W emulsions according to the invention are heated in accordance with the process described in W/O 93/11865, after formation of the multiple droplets, to a temperature above the PIT, they are converted into O/W emulsions.

The following examples relate to advantageous embodiments according to the invention. The numerical values are always percentages by weight, based on the total weight of the formulations, unless expressly noted otherwise.

EXAMPLE 1

| | |
|---|---|
| PEG 100-stearate | 2.00% |
| glyceryl stearate | 4.00% |
| squalane | 1.50% |
| squalene | 1.50% |
| isopropyl palmitate | 5.40% |
| magnesium sulphate | 0.60% |
| preservative | 0.50% |
| water, completely desalinated, to | 100.00% |

The fatty phase, which comprises the emulsifier, is heated to 80° C., and the aqueous phase likewise. The two phases are combined with one another at 80° C. homogenized for about 3–10 minutes and then cooled to room temperature.

EXAMPLE 2

| PEG 40-stearate | 1.00% |
|---|---|
| glyceryl stearate | 2.00% |
| cetyl alcohol | 3.00% |
| mineral oil DAB 9 | 2.00% |
| safflower oil | 2.00% |
| isopropyl palmitate | 4.50% |
| glycerol | 3.00% |
| magnesium sulphate | 1.20% |
| preservative | 0.50% |
| water, completely desalinated to | 100.00% |

The fatty phase, which comprises the emulsifier, is heated to 80° C., and the aqueous phase likewise. The two phases are combined with one another at 80° C., homogenized for about 3–10 minutes and then cooled to room temperature.

EXAMPLE 3

| PEG 80-stearate | 2.00% |
|---|---|
| cetyl alcohol | 3.00% |
| mineral oil DAB 9 | 1.50% |
| evening primrose oil | 2.50% |
| isopropyl palmitate | 5.40% |
| propylene glycol | 3.00% |
| potassium chloride | 0.60% |
| preservative | 0.50% |
| water, completely desalinated, to | 100.00% |

The fatty phase, which comprises the emulsifier, is heated to 80° C., and the aqueous phase likewise. The two phases are combined with one another at 80° C., homogenized for about 3–10 minutes and then cooled to room temperature.

EXAMPLE 4

| Steareth-100 | 2.00% |
|---|---|
| myristyl alcohol | 1.00% |
| mineral oil DAB 9 | 3.00% |
| castor oil | 3.00% |
| cyclomethicone | 2.00% |
| propylene glycol | 3.00% |
| glycerol | 5.00% |
| potassium chloride | 3.00% |
| preservative | 0.50% |
| water, completely desalinated to | 100.00% |

The fatty phase, which comprises the emulsifier, is heated to 80° C., and the aqueous phase likewise. The two phases are combined with one another at 80° C., homogenized for about 3–10 minutes and then cooled to room temperature.

EXAMPLE 5

| Steareth-20 | 2.00% |
|---|---|
| cetearyl alcohol | 3.00% |
| vaseline | 0.50% |
| wheatgerm oil | 1.50% |
| dimethicone | 5.00% |
| glycerol | 5.00% |
| sodium chloride | 3.00% |
| preservative | 0.50% |
| water, completely desalinated to | 100.00% |

The fatty phase, which comprises the emulsifier, is heated to 80° C., and the aqueous phase likewise. The two phases are combined with one another at 80° C. homogenized for about 3–10 minutes and then cooled to room temperature.

EXAMPLE 6

| Dimethicone copolyol | 2.00% |
|---|---|
| cetearyl alcohol | 3.00% |
| vaseline | 0.50% |
| wheatgerm oil | 1.50% |
| dimethicone | 5.00% |
| glycerol | 5.00% |
| sodium chloride | 3.00% |
| preservative | 0.50% |
| water, completely desalinated to | 100.00% |

The fatty phase, which comprises the emulsifier, is heated to 80° C., and the aqueous phase likewise. The two phases are combined with one another at 80° C., homogenized for about 3–10 minutes and then cooled to room temperature.

EXAMPLE 7

| PEG 20-behenate | 2.00% |
|---|---|
| stearyl alcohol | 3.00% |
| vaseline | 1.00% |
| grapeseed oil | 3.00% |
| dimethicone | 3.00% |
| sorbitol | 5.00% |
| zinc sulphate | 3.00% |
| preservative | 0.50% |
| water, completely desalinated to | 100.00% |

The fatty phase, which comprises the emulsifier, is heated to 80° C., and the aqueous phase likewise. The two phases are combined with one another at 80° C., homogenized for about 3–10 minutes and then cooled to room temperature.

EXAMPLE 8

| Decaglyn 1-IS | 2.00% |
|---|---|
| stearyl alcohol | 3.00% |
| vaseline | 1.00% |
| grapeseed oil | 3.00% |
| dimethicone | 3.00% |
| sorbitol | 5.00% |
| zinc sulphate | 3.00% |
| preservative | 0.50% |
| water, completely desalinated to | 100.00% |

The fatty phase, which comprises the emulsifier, is heated to 80° C., and the aqueous phase likewise. The two phases are combined with one another at 80° C., homogenized for about 3–10 minutes and then cooled to room temperature.

EXAMPLE 9

| PEG 20-myristate | 2.00% |
|---|---|
| stearyl alcohol | 3.00% |
| vaseline | 2.00% |
| castor oil | 5.00% |
| dimethicone | 5.00% |
| sorbitol | 5.00% |
| zinc sulphate | 3.00% |
| preservative | 0.50% |
| water, completely desalinated to | 100.00% |

The fatty phase, which comprises the emulsifier, is heated to 80° C., and the aqueous phase likewise. The two phases

EXAMPLE 10

| | |
|---|---|
| Sucrose laurate | 2.00% |
| stearyl alcohol | 3.00% |
| vaseline | 2.00% |
| castor oil | 5.00% |
| dimethicone | 5.00% |
| sorbitol | 5.00% |
| zinc sulphate | 3.00% |
| preservative | 0.50% |
| water, completely desalinated to | 100.00% |

The fatty phase, which comprises the emulsifier, is heated to 80° C., and the aqueous phase likewise. The two phases are combined with one another at 80° C., homogenized for about 3–10 minutes and then cooled to room temperature.

EXAMPLE 11

| | |
|---|---|
| PEG 80-behenate | 2.00% |
| glyceryl behenate | 4.00% |
| squalane | 3.00% |
| castor oil | 5.40% |
| glycerol | 6.00% |
| magnesium sulphate | 2.60% |
| preservative | 0.50% |
| water, completely desalinated to | 100.00% |

The fatty phase, which comprises the emulsifier, is heated to 80° C., and the aqueous phase likewise. The two phases are combined with one another at 80° C., homogenized for about 3–10 minutes and then cooled to room temperature.

We claim:

1. Multiple emulsions of the W/O/W type consisting of a continuous external aqueous phase, an oily phase dispersed therein and a second (internal) aqueous phase dispersed in this oily phase, comprising,
   (a) at least one emulsifier (emulsifier A), chosen from the group consisting of emulsifiers, the lipophilicity of which increases with increasing temperature and the hydrophilicity of which increases with decreasing temperature, the emulsifier or emulsifiers changing from an HLB value <10 to an HLB value >10 in the temperature range of 40°–90° C., the HLB value of the emulsifier or emulsifiers at room temperature being between 11 and 18, and the emulsifier not being completely soluble in the oily phase when the oily phase is combined with the aqueous phase,
   (b) an oily phase, the base constituents of the oily phase being chosen from the group consisting of physiologically tolerated oils, fats and waxes, where
      the single base constituent of the oily phase, if this comprises only a single oil component, or
      the combination of the base constituents of the oily phase, if the oily phase comprises several oil components has a "required HLB value" (RLBH) of 10–20, and/or a polarity, (determined in units of surface tension) of less than 30 mN/m,
   (c) an external and an internal aqueous phase, these aqueous phases comprising from about 0.3–8% by weight (based on the total composition) of physiologically tolerated organic and/or inorganic electrolytes with mono-, di- or trivalent cations,
   (d) if desired further auxiliaries and/or additives, the chief purpose of which is to stabilize the multiple emulsion droplets, after in situ formation thereof, and which can be incorporated into the oily phase and/or the aqueous phases, and
   (e) if desired other bases, auxiliaries, additives and/or active compounds customary in cosmetics or medical galenics, which can be incorporated into the oily phase and/or the aqueous phases.

2. Emulsions according to claim 1, wherein the emulsifier or emulsifiers A are chosen from the group consisting of emulsifiers of the general formula

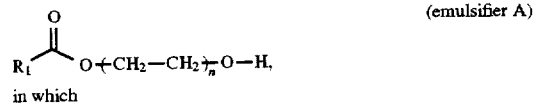

(emulsifier A)

in which $R^1 = C_{10}-_{30}$-alkyl and
n=a number from 8 to 200.

3. Emulsions according to claim 2, wherein the emulsifier or emulsifiers A are chosen from the group in which n assumes values of 20 to 40.

4. Emulsions according to claim 1, wherein the emulsifier or emulsifiers A are chosen from the group consisting of
   (a) mixtures of lecithin, fatty alcohols and fatty acids,
   (b) sucrose laureate,
   (c) polyglycerol mono-fatty acid esters, and
   (d) dimethicone copolyols.

5. Emulsions according to claim 4, wherein said emulsifier is poloyglycerol isostearate.

6. Emulsions according to claim 4, wherein said emulsifier is decaglyceryl monoisostearate.

7. Emulsions according to claim 1, comprising one or more stabilizers of the general formula

(stabilizer 1)

in which one of the radicals X or Y is a hydrogen atom and the remaining radical Y or X is chosen from the group consisting of branched or unbranched acyl radicals having 10–30 carbon atoms.

8. Emulsions according to claim 7, wherein glycerol monostrearate is chosen as stabilizer 1.

9. Emulsions according to claim 7, wherein the emulsifier or emulsifiers A and/or the stabilizer or stabilizers 1 are employed in concentrations of 0.05–15.0% by weight, in each case based on the total weight of the formulations.

10. Emulsions according to claim 7, wherein said emulsifier or emulsifiers and/or stabilizer or stabilizers are employed in concentration of 0.1–7% by weight.

11. Emulsions according to claim 7, wherein said emulsifier or emulsifiers and/or stabilizer or stabilizers are employed in concentration of 0.5–5% by weight.

12. Emulsions according to claim 1, wherein the oily phase is chosen from the group consisting of oils of the plant families Euphorbiaceae, Poaceae, Fabaceae, Brassicaceae, Pedalaceae, Asteraceae, Linaceae, Flacourticaceae, and Violales.

13. Emulsions according to claim 1, wherein the oily phase is chosen from the group consisting of oil components which have a polarity of between 10 and 30 mN/m.

14. Emulsions according to claim 1, wherein the oil components are choosen from the group consisting of oils which have a polarity of between 10 and 20 mN/m.

15. Emulsions according to claim 1, wherein one or more branched and/or unbranched aliphatic fatty alcohols and/or fatty acids having 8 to 18 carbon atoms are incorporated into the oily phase.

16. Emulsions according to claim 1, wherein the oily phase comprises no components which have a melting point below 40° C.

17. Emulsions according to claim 1, wherein electrolytes are added to the aqueous phase in concentrations of from about 0.3–5.0% by weight based on the total weight of the formulation.

18. Emulsions according to claim 1, wherein the HLB value of the emulsifier or emulsifier is between 13 and 14.

19. Emulsions according to claim 1, wherein the oily phase is selected from the group consisting of naturally occurring castor oil, wheatgerm oil, grapeseed oil, coconut oil, safflower oil, thistle oil, evening primrose oil and other oils which comprise at least 1.5% by weight of linoleic acid glycerides.

20. Emulsions according to claim 16, wherein the electrolyte is sodium chloride.

21. Emulsions according to claim 1, wherein the electrolytes are added to the aqueous phase in concentrations of 0.6–3% by weight.

22. Process for the preparation of W/O/W emulsions, wherein water containing from about 0.3–8% by weight (based on the total composition) of physiologically tolerated organic and/or inorganic electrolytes having mono- and/or divalent cations, and an oily phase, this oily phase comprising (a) at least one emulsifier (emulsifier A), chosen from the group consisting of emulsifiers, of which the lipophilicity increases with increasing temperature and the hydrophilicity of which increases with decreasing temperature, the emulsifier or emulsifiers changing from an HLB value <10 to an HLB value >10 in the temperature range of 40°–°90° C., the HLB value of the emulsifier or emulsifiers at room temperature being between 11 and 18, and the emulsifier not being completely soluble in the oily phase at about 80° C., said emulsifier comprising at least one emulsifier of the general formula

 (emulsifier A)

in which $R^1=C_{10-30}$-alkyl and n=a number from 8 to 200, (b) if desired furthermore, comprising:

(b1) one or more stabilizers of the general formula

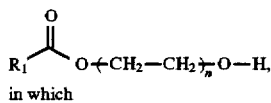 (stabilizer 1)

in which one of the radicals X and Y is a hydrogen atom and the remaining radical Y or X is chosen from the group consisting of branched or unbranched acyl radicals having 10–30 carbon atoms, and/or (b2) one or more branched and/or unbranched aliphatic fatty alcohols having 8 to 18 carbon atoms, (c) the base components of this oily phase, which are chosen from the group consisting of physiologically tolerated oils, fats and waxes, where the single base constituent of the oily phase, if this comprises only a single oil component, or the combination of the base constituents of the oily phase, if the oily phase comprises several oil components has a "required HLB value (RHLB) of 10–20, and/or a polarity (determined in units of surface tension) of less than 30 mN/m are brought together at a temperature at which the oily phase and the aqueous phase are essentially in liquid form, and the mixture thus formed is agitated constantly and if appropriate subjected to one or more homogenizing steps, and the W/O/W emulsion thus formed is then allowed to cool to room temperature.

23. Process according to claim 22, wherein the W/O/W emulsion is prepared at a temperature above the PIT and is then brought to a temperature below the PIT.

24. Process according to claim 22, wherein the HLB of said emulsifier or emulsifiers ranges between 13 and 14.

25. Process according to claim 22, wherein the aliphatic fatty alcohol in (b2) is cetyl alcohol.

* * * * *

UNITED STATES PATENT AND TRADEMARK OFFICE
CERTIFICATE OF CORRECTION

PATENT NO. : 5,750,124
DATED : May 12, 1998
INVENTOR(S) : Gohla, et al.

It is certified that error appears in the above-identified patent and that said Letters Patent is hereby corrected as shown below:

Col. 16, Claim 8, Line 2      After " glycerol " delete " monostrearate " and substitute --- monostearate ---

Signed and Sealed this

Fourteenth Day of December, 1999

*Attest:*

Q. TODD DICKINSON

*Attesting Officer*      *Acting Commissioner of Patents and Trademarks*